United States Patent [19]

Haag et al.

[11] Patent Number: 5,177,281
[45] Date of Patent: Jan. 5, 1993

[54] DOUBLE BOND ISOMERIZATION OF 1-OLEFIN CONTAINING FEEDS USING ZSM-22, ZSM-23 OR ZSM-35

[75] Inventors: Werner O. Haag, Lawrenceville, N.J.; Jose G. Santiesteban, Yardley, Pa.

[73] Assignee: Mobil Oil Corporation, Fairfax, Va.

[21] Appl. No.: 813,718

[22] Filed: Dec. 27, 1991

[51] Int. Cl.$^5$ ............................ C07C 1/00; C07C 5/23
[52] U.S. Cl. .................................. 585/324; 585/664; 585/666; 585/670
[58] Field of Search ................ 585/664, 666, 670, 324

[56] References Cited

U.S. PATENT DOCUMENTS

| | | | |
|---|---|---|---|
| 2,804,490 | 8/1957 | Beldon | 260/683.4 |
| 3,800,003 | 3/1974 | Sobel | 260/683.49 |
| 4,727,203 | 2/1988 | Hamilton, Jr. | 585/666 |
| 4,749,819 | 6/1988 | Hamilton, Jr. | 585/670 |
| 4,918,255 | 4/1990 | Chou et al. | 585/331 |
| 5,043,520 | 8/1991 | Hamilton, Jr. | 585/666 |

FOREIGN PATENT DOCUMENTS 0129899  1/1985  European Pat. Off. .
0247802  12/1987  European Pat. Off. .

*Primary Examiner*—Patrick P. Garvin
*Assistant Examiner*—E. D. Irzinski
*Attorney, Agent, or Firm*—Alexander J. McKillop; Charles J. Speciale; Laurence P. Hobbes

[57] ABSTRACT

A method for isomerizing a 1-olefin-containing organic feedstock having an average carbon number of about 4 to 5, e.g., 1-butene, to convert 1-olefin to 2-olefin at temperatures less than 200° C., with a double bond isomerization catalyst comprising a zeolite sorbing 30 to 55 mg n-hexane at 90° C., 83 torr, and 15 to 40 mg 3-methylpentane at 90° C., 90 torr, per g dry zeolite in the hydrogen form, e.g., ZSM-22, ZSM-23, or ZSM-35. Catalyst aging is minimal despite operation at low temperatures and high pressures.

21 Claims, No Drawings

DOUBLE BOND ISOMERIZATION OF 1-OLEFIN CONTAINING FEEDS USING ZSM-22, ZSM-23 OR ZSM-35

FIELD OF THE INVENTION

This invention relates to a highly selective method for the conversion of 1-olefin containing hydrocarbon streams to 2-olefin rich product streams. The process uses a catalyst composition comprising a zeolite selected from ZSM-22, ZSM-23, or ZSM-35 to obtain high 1-olefin to 2-olefin selectivities while minimizing catalyst aging.

BACKGROUND OF THE INVENTION

The demand for 2-olefin rich feeds has recently increased. For example, 2-butene-rich feeds have been found to be useful in the production of alkylate prepared by alkylation of isoparaffins with light olefins. The desirability of using butene-2 as compared to butene-1 as feedstock to an alkylation zone to produce high octane gasoline blending stocks is disclosed in U.S. Pat. No. 2,804,490. U.S. Pat. No. 3,800,003 presents a process in which a feed stream comprising butene isomers is passed into an isomerization zone to increase the quantity of butene-2 available for passage into a downstream alkylation zone. U.S. Pat. No. 4,918,255 discloses an alkylation process using a heterogeneous isoparaffin/olefin alkylation catalyst, e.g. $BF_3/Al_2O_3$, wherein the olefin feed is isomerized to reduce alpha olefin content using as isomerization catalyst alumina, silica, zirconia, chromium oxide, boron oxide, thoria, magnesia, aluminum sulfate or combinations thereof, as well as boron halide-modified metal oxide.

Double bond isomerization of olefins such as butene in the presence of catalysts of the pentasil type such as ZSM-5 and ZSM-11 at temperatures of 100 to 500° c is disclosed in European Patent Application 0 129 899 to Hoelderich.

European Patent Application 0 247 802, to Barri et al. discloses restructuring olefins using tectometallosilicates of the Theta-1 type (ZSM-22) as well as ZSM-23 at relatively high reaction temperatures of 200 to 550° C. Table 4 thereof shows 1-butene to 2-butene selectivity (mol/mol) of Theta-1 catalyst in the conversion of 1-butene of 92.1% at 234° C. at 100 MPa pressure using an 11.5±2.8% vol/vol 1-butene in nitrogen feed. By-products, especially isobutylene, are formed with a selectivity of 7.9%. The composition of the linear butenes in the product is 16% 1-butene and 84% 2-butene.

U.S. Pat. No. 4,749,819 to Hamilton, Jr. exemplifies double bond isomerization of an alpha olefin feed (preferably $C_{12}$ to $C_{18}$) to produce a product having interior double bond isomerization using a ferrierite catalyst. The reference further teaches at column 5, lines 15 to 19, that "[o]ther aluminosilicates may be exemplified by ZSM-12, ZSM-22, ZSM-23 and ZSM-48." It is not unexpected that a wide variety of catalysts can be used to isomerize 1-butene at high initial activity inasmuch as the double bond shift is one of the most facile among the hydrocarbon reactions. The thermodynamics of the reaction indicate that enhanced selectivity for 2-butenes occurs at lower temperatures and that relatively great selectivities are possible with a wide variety of catalysts at such temperatures. However, catalyst stability is known to decrease as temperatures are lowered. At lower temperatures, zeolite isomerization catalysts are known to "age" or lose their high level of activity with time. This has been attributed to the formation of undesirable carbonaceous deposits or "coke" on the catalyst's active sites during hydrocarbon conversion reactions. Once the carbon deposits have reached the point where the reaction level becomes economically undesirable, the only known way to correct the problem has been to shut down the reactor and burn the carbon off of the catalyst in an oxygen-containing atmosphere. This, needless to say, is an expensive operation which should be avoided unless absolutely necessary.

Accordingly, it would be desirable to provide a method for isomerizing 1-olefin feeds to 2-olefin rich products over a catalyst which exhibits not only high 1-olefin conversion and 2-olefin selectivity, but high stability at low temperatures as well. It would also be desirable to provide an isomerization method which not only has high selectivity for 1-olefin to 2-olefin, but a low rate of catalyst deactivation as well, resulting in long cycle times between catalyst regeneration.

SUMMARY OF THE INVENTION

The present invention relates to a method for isomerizing a 1-olefin-containing organic feedstock to provide a 2-olefin rich product. The method comprises contacting the feedstock under double bond isomerization conditions which include temperatures less than 200° C., with a double bond isomerization catalyst comprising a zeolite. The method is characterized by reduced catalyst aging which is achieved by selecting as the zeolite one sorbing 30 to 55 mg n-hexane at 90° C., 83 torr, and 15 to 40 mg 3-methylpentane at 90° C., 90 torr, per g dry zeolite in the hydrogen form; and selecting as said feedstock one having an average carbon number of about 4 to 5. Suitable zeolites for the present method include those selected from the group consisting of zeolites having the framework structure of ZSM-22, ZSM-23, and ZSM-35. Examples of suitable 1-olefin include 1-butene, 1-pentene and 3-methyl-1-butene.

In another aspect, the present invention relates to a method for isomerizing a 1-olefin-containing organic feedstock to provide a 2-olefin rich product which comprises contacting said feedstock under double bond isomerization conditions, at temperatures less than 200° C., with a double bond isomerization catalyst comprising a zeolite; said method being characterized by reduced catalyst aging by selecting as said zeolite one having a Pore Size Index of 20 to 26; and selecting as said feedstock one having an average carbon number of about 4 to 5.

The present invention utilizes a group of catalysts which are uniquely suited to use in double bond isomerization of organic feeds having an average carbon number of 4 to 5. Such catalysts exhibit high activity at low temperatures (less than 200° C.). They are capable of isomerizing 1-butene-containing feeds to a mixture of n-butenes containing greater than 85% 2-butenes and less than 15% 1-butene. They can operate at a high pressure, e.g. 1 atmosphere or greater. Finally, such catalysts maintain high activity for an extended period under conditions of low temperature and high pressure.

DETAILED DESCRIPTION OF THE INVENTION

The present invention relates to a method for isomerizing a 1-olefin-containing organic feedstock to convert a substantial portion of said 1-olefin, e.g., 1-butene, to 2-olefin, e.g., 2-butene, by contacting the feedstock under double bond isomerization conditions, at temperatures less than 200° C. The isomerizing method of the present invention can be carried out at temperatures of 20 to 150° C., preferably 50 to 130° C., weight hourly space velocities of said feedstock based on total feed between 0.5 and 100 $hr^{-1}$, preferably between 1 and 80 $hr^{-1}$; total pressure between 100 and 10000 kPa, preferably between 300 and 6000 kPa, to yield at least 85 wt % 2-olefin, preferably at least 88 wt % 2-olefin, in the olefinic product, and less than 15 wt%, preferably less than 12 wt % oligomeric product. The catalyst employed under the conditions of the present invention has a catalyst stability parameter (CSP) of greater than 375, preferably greater than 800.

The CSP describes the useful cycle life of the catalyst, expressed in kg feed processed per kg catalyst. The useful cycle life is reached when the composition of the olefinic product drops to less than 85% 2-olefins. The catalyst can then be regenerated by conventional means, such as hydrogen regeneration or oxidative combustion of carbonaceous deposits.

Although the present method can be carried out with the feed in the gaseous state, it is preferably carried out in the liquid phase in order to avoid costly and uneconomical vaporization and condensation steps. In order to assure liquid phase operation and to keep the pressure at acceptably low limits, the temperature is preferably kept below the critical temperature of the butenes, which is about 146° C.

The 2-olefin rich stream resulting from the isomerization method of the present invention can be utilized as the olefin stream in isoparaffin-light olefin alkylation. The alkylate made therefrom is an especially valuable component of the gasoline pool as it possesses both high research and motor octane numbers.

More particularly, the present invention may be incorporated into a continuous integrated process for producing alkylate from isoparaffin and olefins wherein the present method of isomerization provides a product used as an olefins source for alkylation. The alkylate thus prepared exhibits high quality based on both research and motor octane numbers and as such is particularly well suited for blending into the gasoline pool.

Catalyst

The preferred catalysts, exemplified by ZSM-22, ZSM-23, and ZSM-35, are members of a unique class of zeolites. They have channels described by 10-membered rings of T (=Si or Al) or oxygen atoms, i.e., they are intermediate pore zeolites, distinct from small pore 8-ring or large pore 12-ring zeolites. They differ, however, from other intermediate pore 10-ring zeolites, such as ZSM-5, ZSM-11, ZSM-57 or stilbite, in having a smaller 10-ring channel. If the crystal structure (and hence pore system) is known, a convenient measure of the channel cross-section is given by the product of the dimensions (in angstrom units) of the two major axes of the pores. These dimensions are listed in the "Atlas of Zeolite Structure Types" by W. M. Meier and D. H. Olson, Butterworths, publisher, Second Edition, 1987. The values of this product, termed the Pore Size Index, are listed in Table A.

TABLE A

| Type | Largest Ring Size | Zeolite | Axes of Largest Channel, Å | Pore Size Index |
|---|---|---|---|---|
| 1 | 8 | Chabazite | 3.8 × 3.8 | 14.4 |

TABLE A-continued

| Type | Largest Ring Size | Zeolite | Axes of Largest Channel, Å | Pore Size Index |
|---|---|---|---|---|
| | | Erionite | 3.6 × 5.1 | 18.4 |
| | | Linde A | 4.1 × 4.1 | 16.8 |
| 2 | 10 | ZSM-22 | 4.4 × 5.5 | 24.2 |
| | | ZSM-23 | 4.5 × 5.2 | 23.4 |
| | | ZSM-35 | 4.2 × 5.4 | 22.7 |
| | | ALPO-11 | 3.9 × 6.3 | 24.6 |
| 3 | 10 | ZSM-5 | 5.3 × 5.6 | 29.1 |
| | | ZSM-11 | 5.3 × 5.4 | 28.6 |
| | | Stilbite | 4.9 × 6.1 | 29.9 |
| | | ZSM-57 (10) | 5.1 × 5.8 | 29.6 |
| 4 | 12 | ZSM-12 | 5.5 × 5.9 | 32.4 |
| | | Mordenite | 6.5 × 7.0 | 45.5 |
| | | Beta (C-56) | 6.2 × 7.7 | 47.7 |
| | | Linde-L | 7.1 × 7.1 | 50.4 |
| | | Mazzite (ZSM-4) | 7.4 × 7.4 | 54.8 |
| | | $ALPO_4$-5 | 7.3 × 7.3 | 53.3 |

It can be seen that small pore, eight-ring zeolites have a Pore Size Index below about 17, the intermediate pore, 10-ring zeolites of about 22–30, and large pore, 12-ring zeolites above about 32. It is also apparent, that the 10-ring zeolites are grouped in two distinct classes; Type 2 with a Pore Size Index between about 22.7 and 24.6, and more broadly between about 20 and 26, and Type 3 with a Pore Size Index between 28.6 and 29.9, or more broadly, between about 28 and 31.

The zeolite useful for this invention are those of Type 2 with a Pore Size Index of 20–26.

Alternatively, these zeolites can be distinguished from Type 1 and Type 3 zeolites by their sorption characteristics. Equilibrium sorption data are listed in Table B below. While both Type 2 and Type 3 zeolites sorb more than about 40 mg n-hexane per gram zeolite, the Type 2 zeolites sorb less than 40 mg 3-methylpentane under the conditions specified, in contrast to Type 3 zeolites. Small pore, 8-ring zeolites sorb less than 15 mg of 3-methylpentane per gram of zeolite.

The equilibrium sorption are obtained most conveniently in a thermogravimetric balance by passing a stream of inert gas such as helium containing the hydrocarbon with the indicated partial pressure over the dried zeolite sample held at 90 C for a time sufficient to obtain a constant weight.

This method of characterizing the Type 2 zeolites has the advantage that it can be applied to new zeolites whose crystal structure has not yet been determined. For mixtures of zeolites with amorphous material or for poorly crystallized samples, the numbers apply only to the crystalline portion.

Thus, zeolites useful for the present invention sorb 30 to 55 mg n-hexane and 15 to 40 mg 3-methylpentane per g dry zeolite in the hydrogen form.

TABLE B

| Equilibrium Sorption Data of Medium Pore Zeolites | | | |
|---|---|---|---|
| | | Amount sorbed, mg per g zeolite | |
| Type | Zeolite | n-Hexane[a] | 3-Methylpentane[b] |
| 2 | ZSM-22 | 40 | 20 |
| | ZSM-23 | 45 | 25 |
| | ZSM-35 | 50 | 25 |
| 3 | ZSM-5 | 103 | 61 |
| | ZSM-12 | 52 | 58 |
| | ZSM-57 | 60 | 70 |
| | MCM-22 | 89 | 79 |

[a] at 90° C., 83 torr n-hexane
[b] at 90° C., 90 torr 3-methylpentane

ZSM-22 is more particularly described in U.S. Pat. No. 4,556,477, the entire contents of which are incorporated herein by reference. ZSM-22 and its preparation in microcrystalline form using ethylpyridinium as directing agent are described in U.S. Pat. No. 4,481,177 to Valyocsik, the entire contents of which are incorporated herein by reference. For purposes of the present invention, ZSM-22 is considered to include its isotypes, e.g., Theta-1, Gallo-Theta-1, NU-10, ISI-1, and KZ-2.

ZSM-23 is more particularly described in U.S. Pat. No. 4,076,842, the entire contents of which are incorporated herein by reference. For purposes of the present invention, ZSM-22 is considered to include its isotypes, e.g., EU-13, ISI-4, and KZ-1.

ZSM-35 is more particularly described in U.S. Pat. No. 4,016,245, the entire contents of which are incorporated herein by reference. For purposes of the present invention, ZSM-35 is considered to include its isotypes, e.g., ferrierite, FU-9, ISI-6, NU-23, and Sr-D.

The zeolite catalyst used is preferably at least partly in the hydrogen form, e.g., HZSM-22, HZSM-23, or HZSM-35. Other metals or cations thereof, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g. by heating at over 500° C. for 1 hour or more. The hydrogen form can then be obtained by base exchange with ammonium salts followed by calcination, e.g. at 500° C. in air.

The catalysts employed in the present invention may also contain divalent or trivalent metal cations, preferably in amounts ranging from 0 to 3 wt %, more preferably from 0 to 2 wt %.

The metal may be incorporated into the catalyst by any suitable method such as impregnation or exchange onto the zeolite. The metal may be incorporated in the form of a cationic, anionic or a neutral complex, such as $Pt(NH_3)_4^{2+}$, and cationic complexes of this type are found convenient for exchanging metals onto a zeolite. Anionic complexes are also useful for impregnating metals into the zeolites.

Among the divalent metals suited to incorporation into the catalyst are those of Group IIA, e.g., Mg, Ca and Sr. Suitable trivalent metals include Fe, Al and the lanthanides. Included among the suitable divalent and trivalent metals are the Group VIIIA metals of which the noble metals such as Pd, Pt, Rh and Ru are believed particularly suited to use in the present invention. Among the foregoing metals are those which exhibit hydrogenation ability. Incorporation of hydrogenation metals is particularly useful in carrying out simultaneous butene isomerization and hydrogenation of dienes, e.g. butadiene, or alkynes such as acetylene.

It is generally desirable to incorporate the zeolite with another material resistant to the temperatures and other conditions employed in organic conversion processes. Such matrix materials include active and inactive materials and synthetic or naturally occurring zeolites as well as inorganic materials such as clays, silica and/or metal oxides. The latter may be either naturally occurring or in the form of gelatinous precipitates, sols or gels including mixtures of silica and metal oxides. Use of a material in conjunction with the zeolite, i.e., combined therewith, which is active, tends to improve the conversion and/or selectivity of the catalyst in certain organic conversion processes. However, for present purposes, inactive materials of low acidity such as silica or zirconia are preferred in that they prevent unwanted polymerization reactions engendered by more active materials such as alumina. Inactive materials can also suitably serve as diluents to control the amount of conversion in a given process so that products can be obtained economically and orderly without employing other means for controlling the rate of reaction.

Generally the catalyst of the present invention comprises 2 to 90 wt %, preferably 5 to 50 wt%, e.g., 10 to 30 wt %, of a suitable matrix material.

Frequently, zeolite materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with the zeolite catalyst include the montmorillonite and kaolin family, which families include the sub-bentonites, and the kaolins commonly known as Dixie, McNamee, Georgia and Florida clays or others in which the main mineral constituents is halloysite, kaolinite, dickite, nacrite, or anauxite. Such clays can be used in the raw state as originally mined or initially subjected to calcination, acid treatment or chemical modification.

In addition to the foregoing materials, the zeolite can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

As noted above, of all the foregoing materials, silica is preferred as the matrix material owing to its relative inertness for catalytic polymerization reactions which are preferably minimized in the instant isomerization processes. The relative proportions of finely divided zeolite and inorganic oxide gel matrix vary widely with the zeolite content ranging from about 10 to about 98 percent by weight and more usually in the range of about 50 to about 95 percent by weight of the composite, say about 60 to 90 percent by weight of the composite.

The regeneration of spent zeolite catalyst used in the isomerization reaction is carried out oxidatively or hydrogenatively employing procedures known in the art. The catalyst of the present invention can be readily reactivated without significantly reducing selectivity for 2-olefins by exposing it to hydrogen for a suitable period, e.g., overnight, and temperature to effect reactivation. For example, the deactivated catalyst is heated in a flowing stream of hydrogen-containing gas to a temperature of 250° C. during 1 hour, and kept at 250° C. for 4 hours. Alternatively, the deactivated catalyst is heated to 350° C. in a flowing stream of inert gas such as nitrogen which contains 0.5% $O_2$ until the major exothermic temperature rise has subsided; the oxygen content is then increased stepwise to 1%, 3%, and finally to about 20%, and the temperature increased to 450° C. and held there for 6 hours.

Alpha value, or alpha number, of a zeolite is a measure of zeolite acidic functionality and is more fully described together with details of its measurement in U.S. Pat. No. 4,016,218, *J. Catalysis*, 6, pp. 278–287 (1966) and J. Catalysis, 61, pp. 390–396 (1980). The experimental conditions cited in the latter reference are used for characterizing the catalyst described herein. The zeolite catalyst of the present invention has an alpha value ranging from 2 to 300, preferably 5 to 200, based on the zeolite component, when composite catalysts are used.

Feedstream

Suitable organic feeds for the isomerization method of the present invention are those having an average carbon number of about 4 to 5. Such feeds contain 1-olefin, e.g. a $C_3$ to $C_5$ hydrocarbon stream comprising at least 2 wt % 1-olefin, e.g. at least 2 wt % 1-butene or at least 2 wt % 1-pentene. Such feedstocks can include a $C_4$ cut of a cracking process light gas. Such light gas can contain butene isomers in mixture with substantial amounts of paraffins including n-butane and isobutane and preferably contain less than 3 wt % isobutene. Such $C_4$ cuts can be obtained as the isobutylene-depleted $C_4$ effluent stream of an etherification unit wherein methanol and a catalytic cracking $C_4$ cut are reacted to form methyl tert-butyl ether which is separated from said effluent stream.

Mixtures containing cis-2-butene and trans-2-butene as well as 1-butene can be used. These mixtures can contain the linear butene isomers in a ratio that differs from the thermodynamic equilibrium ratio prevailing at the isomerization reaction temperature. The $C_4$ components usually contain a major amount of unsaturated compounds, such as 5–40% isobutylene, 20–55% linear butenes, and small amounts of butadiene.

The following table lists the thermodynamic linear butene isomer distribution from the thermodynamic data given in The *Chemical Thermodynamics of Organic Compounds*, D. R. Stull, E. F. Westrum, Jr., and G. C. Sinke, John Wiley & Sons, New York, 1969.

TABLE 1

| Temperature, °C. | Percent Composition | |
|---|---|---|
|  | 1-Butene | 2-Butene |
| 25 | 2.6 | 97.4 |
| 100 | 6.0 | 94.0 |
| 200 | 10.4 | 89.6 |
| 300 | 15.4 | 84.6 |
| 400 | 20.1 | 79.9 |
| 500 | 24.3 | 75.7 |
| 600 | 28.0 | 72.0 |

The 1-butene-containing feed may also contain 2-butene, isobutylene, n-butane and/or isobutane, as well as $C_1$-$C_3$ and $C_{5+}$ hydrocarbons. In general, it is contemplated to use a stream comprising at least 15%, and preferably at least 25% butenes. Especially preferred feeds are the $C_4$ fractions obtained from catalytic cracking of gas oil, from coking of resid and from steam cracking of naphtha. In one embodiment, the organic feedstock is a $C_4$ cut of a cracking process light gas and contains about 10 wt % 1-butene.

Two typical compositions of commercial FCC $C_4$ cuts are set out in Table 2 below.

TABLE 2

|  | Feed 1 Wt % | Feed 2 Wt % of | | |
|---|---|---|---|---|
|  | Total | Total | Olefins | Linear Olefins |
| n-$C_4$ | 19.7 | 6.1 | — | — |
| i-$C_4$ | 46.0 | 29.3 | — | — |
| i-$C_4$ = | 5.9 | 19.5 | 30.2 | — |
| 1-$C_4$ = | 9.0 | 15.8 | 24.4 | 34.9 |
| 2-tr-$C_4$ = | 11.2 | 17.1 | 26.5 | 38.0 |
| 2-cis-$C_4$ = | 8.2 | 12.2 | 18.9 | 27.1 |
|  | 100.0 | 100.0 | 100.0 | 100.0 |

In view of the desirability of carrying out the isomerization with a feed which comprises minimal isobutene, a preferred feed is the effluent of a liquid phase iso-olefin etherification reactor which employs alkanol and $C_4$ or $C_{4+}$ hydrocarbon feedstock, from which the alkyl tert-butyl ether product is separated out. Inasmuch as isobutene is reacted at nearly quantitative levels in this etherification, the effluent contains only small amounts of isobutene, e.g., less than 3 or even less than 1 wt % isobutene.

$C_{4+}$ heavier olefinic hydrocarbon streams may be used. Preferred is a $C_5$ cut containing 1-pentene, 2-pentene, isopentene, pentane and isopentane. Other suitable feedstocks include a $C_5$ cut of a cracking process light gasoline, e.g., one as the isopentene-depleted $C_5$ effluent stream of an etherification unit wherein methanol and a catalytic cracking $C_5$ cut are reacted to form methyl tert-amyl ether which is separated from said effluent stream.

U.S. Pat. No. 4,605,787 to Chu et al., provides an example of etherification of isobutene with methanol. It can be carried out in the vapor phase at temperatures between 77° C. and 105° C. in contact with acidic ZSM-5 or ZSM-11 to produce MTBE in high conversion and selectivity. This patent is incorporated herein by reference as an example of suitable effluent which may be employed as feed to the method of the present invention.

EXAMPLES

Examples 1–7

Isomerization reactions were carried out in a fixed bed flow reactor. The feed of 1-butene was passed at 1 atmosphere pressure over the binder-free catalyst. Products were analyzed by gas chromatography. Temperatures and flow rates, expressed as WHSV=g feed per g catalyst per hour, are indicated in the Table 3 below which accompanies these Examples.

TABLE 3

| Ex. | Zeolite | $SiO_2$/$Al_2O_3$ | Alpha | T °C. | WHSV | 2-$C_4$ = (wt %) |
|---|---|---|---|---|---|---|
| 1 | ZSM-5 | 650 | — | 120 | 18.6 | 17 |
| 2 | ZSM-5 | 70 | — | 120 | 18.6 | 92 |
| 3 | ZSM-48 | 380 | — | 125 | 19.1 | 90 |
| 4 | ZSM-22 | 73 | 60 | 125 | 36.3 | 92 |
| 5 | ZSM-23 | 150 | 18 | 120 | 18.6 | 92 |
| 6 | ZSM-34 | 10 | — | 133 | 18.6 | 84 |
| 7 | ZSM-35 | — | 96 | 122 | 37.4 | 92 |

The ZSM-22 catalyst of Example 4 was synthesized by charging the following to an autoclave: Deionized $H_2O$ (106 parts), $Al_2(SO_4)_3$ (2.2 parts), KOH (45%, 11.1 parts), Ultrasil (18.0 parts), ethylpyridinium bromide (SWAC, 50% aqueous solution, 8.0 parts), and ZSM-22 seeds. The mixture was aged at 200° F. for 18 hours at 90 rpm then crystallized at 320° F. while stirring at 180 rpm for 78 hours. The composition of the reactant gel is described in molar quantities as follows:

| | |
|---|---|
| SiO$_2$Al$_2$O$_3$ | 73 |
| OH/SiO$_2$ | 0.23 |
| N/SiO$_2$ | 0.07 |
| H$_2$O/SiO$_2$ | 23 |
| N/Al$_2$O$_3$ | 5.4 |
| OH/H$_2$O | 0.01 |

The product was water washed, then calcined at 540° C., first in N$_2$ for 3 hours, then full air for another 6 hours, to decompose the organic directing agent. The calcined product was exchanged with NH$_4$NO$_3$ times to remove the potassium. After complete exchange, the product was dried again in air for 3 hours to decompose the NH$_4^+$ leaving the acid form of the zeolite.

The ZSM-23 catalyst of Example 5 was prepared as follows:

157 parts distilled water were charged to an autoclave, followed by 2.33 parts NaOH solution (50% by weight), 1.0 part aluminum sulfate (17.2% Al$_2$O$_3$, and 1.0 part ZSM-23 seeds (100% basis). After mixing thoroughly, 26.4 parts of precipitated silica (HiSil 233 TM) and then 9.33 parts of pyrrolidine were added and mixed thoroughly. The autoclave was heated to 160° C. with stirring and maintained at these conditions until crystallization was complete. The product was identified as ZSM-23 by X-ray diffraction. After flashing the pyrrolidine, the slurry was cooled, filtered, washed, and dried at 120° C. The catalyst was then exchanged with 1 N ammonium nitrate solution (5ml per gram of catalyst) three times at room temperature for 3 hours. The catalyst was rinsed with deionized/distilled water, dried under flowing air at room temperature, and calcined in nitrogen at 538° C. until all the ammonium was removed.

The ZSM-35 catalyst of Example 7 was prepared as follows:

9.42 parts distilled water were charged to an autoclave, followed by 1.38 parts NaOH solution (50% by weight), 1.0 part aluminum sulfate (17.2% Al$_2$O$_3$), 0.03 parts ZSM-35 seeds (100% basis) and 3.20 parts of precipitated silica (HiSil 233 TM) were added with stirring, followed by 1.0 part of pyrrolidine. The autoclave was heated to 105° C. with stirring and the gel crystallized for 74 hours. After flashing the pyrrolidine, the ZSM-35 product was filtered, washed with deionized water, and dried at 120° C. The catalyst was then exchanged with 1 N ammonium nitrate solution (5ml per gram of catalyst) three times at room temperature for 3 hours. The catalyst was rinsed with deionized/distilled water, dried under flowing air at room temperature, and calcined in nirogen at 538° C. until all the ammonium was removed.

All zeolites but the high silica to alumina mole ratio ZSM-5 of Example 1 give close to equilibrium conversions at very high weight hourly space velocities, i.e. short contact time. As noted earlier, the equilibrium composition at about 120° C. has been experimentally determined to be about 92% 2-butene and 8% 1-butene.

Examples 8–13

The following experiments were carried out to assess the aging behavior of various catalysts using the feed and pressure conditions of Examples 1 to 7. Product samples were taken at various times on stream (TOS) as set out below in Table 4 below. All experiments were carried out at 120 to 122° C.

TABLE 4

| | | | % Conv. to 2-C$_4$ = | | | | % Yield | |
|---|---|---|---|---|---|---|---|---|
| Ex. | Zeolite | WHSV | TOS$^b$ | Conv | TOS | Conv | Loss | CSP$^c$ |
| 8 | USY | 5.1 | 0.5 | 74 | 2.2 | 50 | 32 | <2.5 |
| 9 | ZSM-5 (Ex. 2) | 18.6 | 2 | 91 | 20 | 81 | 11 | <372 |
| 10 | ZSM-48 (Ex. 3) | 18.6 | 2 | 15 | 18 | 0.6$^a$ | >96 | <<37 |
| 11 | ZSM-22 (Ex. 4) | 9.9 | 2 | 90 | 36 | 90 | 0 | >>356 |
| 12 | ZSM-23 (Ex. 5) | 18.6 | 2 | 92 | 26 | 92 | 0 | >>484 |
| 13 | ZSM-35 (Ex. 7) | 37.4 | 2 | 92 | 146 | 92 | 0 | >>5460 |

$^a$at 10 WHSV
$^b$TOS = Time on stream, hrs.
$^c$CSP = Catalyst Stability Parameter = kg feed processed per kg catalyst during useful cycle life.

The data show that subtle changes in the pore size and shape have a pronounced effect on the aging characteristics. Both ZSM-22, ZSM-23 and ZSM-35 have a slightly smaller pore opening than ZSM-5 and ZSM-48. In spite of their smaller pore size and contrary to expectations, ZSM-22, ZSM-23, and ZSM-35 have superior aging characteristics compared to ZSM-5.

Example 14

The catalyst of Example 1 (ZSM-5, silica to alumina mole ratio of 650) was tested for aging at 120° C. with WHSV of 1-butene of 18.6 for 2 hours for 43 minutes. The conversion was found to be 3%, down from 17% after 2 minutes on stream, indicating rapid aging.

Example 15

This example demonstrates the double-bond isomerization of 1-butene at high pressure in the liquid phase with a silica-bound ZSM-23 prepared as follows: 65 parts of ZSM-23 were combined with 20 parts of precipitated silica (Ultrasil VN3SP, 100% solids basis) and 15% colloidal silica (Ludox HS-30). Deionized water was added to give an extrudable mull and the mix extruded to 1/16 inch cylindrical extrudate. The extrudate was dried at 121° C., calcined in nitrogen at 538° C. for 2 hours, and then in air for 3 hours. The extrudate was then exchanged with 1N ammonium nitrate solution (5 ml per gram of catalyst) at room temperature for 1 hour. The exchange was repeated 3 times, the extrudate was rinsed with deionized water, dried at 121° C., and calcined in air at 538° C. for 3 hours. The catalyst was then steamed at 398° C. for 24 hours.

The resulting product, in the form of 14–30 mesh particles, was placed into an electrically heated stainless steel tubular reactor. 1-Butene was pumped through the reactor in a downflow mode at a temperature of 120° C., a pressure of 600 psig, and a weight hourly space velocity (WHSV) of 21.5 based on the zeolite component. The composition of butenes in the reactor effluent was 7% 1-butene and 93% 2-butene, corresponding to 100% of the thermodynamic equilibrium.

Example 16

The experiment of Example 15 was repeated with a guard bed preceding the reactor consisting of gamma-alumina, molecular sieve 4A and "oxytrap" sorbent. The following two feed mixtures (in wt%) were used:

| Component | Stream A | Stream B |
|---|---|---|
| Isobutane | 48.0 | 47.8 |
| n-Butane | 20.9 | 20.8 |
| 1-Butene | 10.0 | 10.0 |
| 2-Butene | 21.1 | 21.0 |
| Isobutylene | — | 0.4 |
| | 100.0 | 100.0 |

The results are listed in Table 5. They indicate that excellent butene double isomerization activity was obtained and that the catalyst showed no aging during the 41 days of testing. The isomerization selectivity was in general very good and was further improved when the feed is free of isobutylene.

TABLE 5
Product Distribution Obtained Over ZSM-23/SiO$_2$

| Operating Conditions | | | Time On Stream (days) | Olefin Product Distribution (Wt. %) | | |
|---|---|---|---|---|---|---|
| T (°C.) | WHSV (h$^{-1}$) | Feed | | 1-Butene | 2-Butene | C$_8$= |
| 80 | 6.1 | B | 6 | 4.9 | 91.0 | 4.1 |
| 80 | 3.06 | B | 9 | 3.4 | 91.3 | 5.3 |
| 80 | 12.2 | B | 10 | 8.9 | 87.8 | 3.3 |
| 60 | 2.1 | B | 13 | 6.2 | 89.7 | 4.1 |
| 80 | 6.1 | B | 20 | 5.0 | 90.0 | 4.1 |
| 80 | 3.06 | B | 24 | 3.4 | 91.3 | 5.3 |
| 80 | 6.1 | A | 33 | 5.2 | 93.1 | 1.7 |
| 80 | 3.06 | B | 40 | 3.8 | 90.4 | 5.8 |
| 90 | 6.1 | B | 41 | 5.0 | 90.6 | 4.4 |

At the termination of the experiment after 41 days, the catalyst still showed undiminished activity, gave a C$_4$ olefin product containing 5.2% 1-butene and 94.8% 2-butene, and had processed 5031 kg of feed per kg of catalyst.

Example 17

The experiment of Example 16 was repeated with feed mixture A, except that ZSM-22 was used as the catalyst. At 80° C., 600 psig and a WHSV of 16.7, the reaction product consisted of 6.4 wt % 1-butene and 92.3% wt % 2-butene.

Examples 18–19

These examples set out in Table 6 below illustrate the use of different binders for the zeolite ZSM-23, using the experimental conditions and feed mixture A of Example 16.

TABLE 6

| Binder | Example 18 Alumina | Example 19 Silica |
|---|---|---|
| WHSV | 18.3 | 6.1 |
| Product Distribution, wt % | | |
| 1-Butene | 8.3 | 7.6 |
| 2-Butene | 86.1 | 99.5 |
| Octenes | 5.6 | 0.9 |

It is seen that the use of a silica binder instead of alumina binder results in less octene by-product formation. We expect similar high-selectivity with ZSM-23 bound with other non-acidic binders such as kaolin, zirconia, titania, graphite or with self-bound ZSM-23.

Example 20

In this comparison example, 1-decene, purified by percolation through a column of activated alumina, was passed over the ZSM-23 catalyst of Example 16 at 126° C. and a WHSV=20. The data are listed in Table 7 below. The activity loss is calculated relative to the sample taken at 0.32 hours. on stream and does not include the additional activity loss occurring between 0 and 0.32 hours. It is seen that the catalytic activity decreases significantly within a few hours. From 0.32 to 0.87 hours, the activity dropped to 84%. During this period, only 11 kg of feed were processed per kg of catalyst.

TABLE 7

| Time on Stream (hrs) | % Isomerization | % Activity Loss |
|---|---|---|
| 0.32 | 87 | 0 |
| 0.87 | 73 | 16 |
| 1.33 | 66 | 24 |
| 2.83 | 59 | 32 |
| 17.50 | 40 | 54 |
| 26.12 | 34 | 61 |

Example 21

The isomerization of 1-butene was carried out by passing a mixture of 12 vol % 1-butene in nitrogen at 1 atmosphere pressure over the USY catalyst of Example 12 at a WHSV=9.1 based on olefin at the temperatures indicated with the results listed in Table 8 below.

TABLE 8

| Temp. °C. | 1-Butene conv., % | Selectivity based on 1-butene, wt % | | | |
|---|---|---|---|---|---|
| | | C$_1$—C$_4$ | 2-C$_4$= | i-C$_4$= | C$_5$+ |
| 228 | 89.3 | 0.9 | 94.7 | tr. | 4.4 |
| 236 | 92.0 | 2.6 | 87.8 | tr. | 9.5 |
| 288 | 91.9 | 5.0 | 81.3 | 1.1 | 12.5 |

Example 22

1-Butene isomerization was carried out as described in Examples 1–7; ZSM-12 was used as catalyst at a temperature of 122° C. and WHSV=9. Product samples were taken and analyzed after various times on stream, and are reported in Table 9 below.

TABLE 9

| Time on Stream, min. | C$_4$-olefin Distribution, % | | Yield loss, % |
|---|---|---|---|
| | 1-Butene | 2-Butene | |
| 2 | 13.9 | 86.1 | 0 |
| 53 | 40.1 | 59.9 | 30 |
| 120 | 49.7 | 50.3 | 4 |

This catalyst shows rapid deactivation. By contrast, ZSM-23 shows no aging between 2 min. and 20 hours when tested even at higher flow rate (WHSV=18.2) as shown by Examples 5 and 11.

It is claimed:

1. A method for isomerizing a 1-olefin-containing organic feedstock to provide a 2-olefin rich product which comprises contacting said feedstock under double bond isomerization conditions which include temperatures less than 200° C., with a double bond isomerization catalyst comprising a zeolite; said method being characterized by reduced catalyst aging by selecting as said zeolite one sorbing 30 to 55 mg n-hexane at 90° C., 83 torr, and 15 to 40 mg 3-methylpentane at 90 C, 90 torr, per g dry zeolite in the hydrogen form; and selecting as said feedstock one having an average carbon number of about 4 to 5.

2. The method of claim 1 wherein said zeolite is selected from the group consisting of those having the framework structure of ZSM-22, ZSM-23, and ZSM-35; said isomerizing is carried out at temperatures of 20 to 150° C., weight hourly space velocities of said feedstock based on total feed between 0.5 and 100 hr-1; total pressure between 100 and 10000 kPa to yield at least 85 wt % 2-olefin in the olefinic product and less than 15 wt % oligomeric product; and said catalyst having a catalyst stability parameter of greater than 375.

3. The method of claim 1 wherein said isomerizing is carried out in the liquid phase at temperatures of 50 to 130° C., weight hourly space velocities of said feedstock between 1 and 80 hr$^{-1}$; total pressure between 300 and 6000 kPa to yield at least 88 wt % 2-olefin in the olefinic product and less than 12 wt % oligomeric product; and said catalyst having a catalyst stability parameter of greater than 800.

4. The method of claim 1 wherein said catalyst is reactivated by exposure to hydrogen at temperatures of at least 250° C. for a time sufficient to effect reactivation.

5. The method of claim 1 wherein said zeolite is hydrogen-exchanged.

6. The method of claim 1 wherein said zeolite is cation-exchanged with a divalent or trivalent metal ion.

7. The method of claim 1 wherein said zeolite contains a noble metal.

8. The method of claim 1 wherein said catalyst comprises 2 to 90 wt % of a matrix selected from the group consisting of silica, alumina, zirconia, and silica-alumina.

9. The method of claim 1 wherein said catalyst comprises 5 to 50 wt % of a silica matrix.

10. The method of claim 1 wherein said organic feedstock is a $C_3$ to $C_5$ hydrocarbon stream comprising at least 2 wt % 1-butene.

11. The method of claim 1 wherein said organic feedstock is a $C_3$ to $C_5$ hydrocarbon stream comprising at least 5 wt % 1-pentene.

12. The method of claim 1 wherein said organic feedstock is a $C_4$ cut of a cracking process light gas.

13. The method of claim 1 wherein said organic feedstock is a $C_5$ cut of a cracking process light gasoline.

14. The method of claim 1 wherein said organic feedstock is a $C_4$ cut of a cracking process light gas and contains less than 3 wt % isobutene.

15. The method of claim 1 wherein said organic feedstock is a $C_5$ cut of a cracking process light gasoline and contains less than 6 wt % isopentene.

16. The method of claim 1 wherein said organic feedstock is the isobutylene-depleted $C_4$ effluent stream of an etherification unit wherein methanol and a catalytic cracking $C_4$ cut are reacted to form methyl tert-butyl ether which is separated from said effluent stream.

17. The method of claim 1 wherein said organic feedstock is an isopentene-depleted $C_5$ effluent stream of an etherification unit wherein methanol and a catalytic cracking $C_5$ cut are reacted to form methyl tert-amyl ether which is separated from said effluent stream.

18. The method of claim 1 wherein said zeolite is ZSM-22.

19. The method of claim 1 wherein said zeolite is ZSM-23.

20. The method of claim 1 wherein said zeolite is ZSM-35

21. A method for isomerizing a 1-olefin-containing organic feedstock to convert a substantial portion of said 1-olefin to 2-olefin which comprises contacting said feedstock under double bond isomerization conditions, at temperatures less than 200° C., with a double bond isomerization catalyst comprising a zeolite; said method being characterized by reduced catalyst aging by selecting as said zeolite one having a Pore Size Index of 20 to 26, and selecting as said feedstock one having an average carbon number of about 4 to 5.

* * * * *